United States Patent [19]

Goto et al.

[11] Patent Number: 5,605,920
[45] Date of Patent: Feb. 25, 1997

[54] TETRAZOLINONES

[75] Inventors: Toshio Goto, Shimotsuga-gun; Yoshinori Kitagawa, Tochigi; Seishi Ito, Oyama; Katsuhiko Shibuya, Tochigi; Tatsuya Yamaoka, Tochigi; Chieko Ueno, Tochigi; Yoshiko Kyo, Tochigi, all of Japan

[73] Assignee: Nihon Bayer Agrochem K.K., Tokyo, Japan

[21] Appl. No.: 618,954

[22] Filed: Mar. 20, 1996

[30] Foreign Application Priority Data

Mar. 23, 1995 [JP] Japan .................................. 7-088619

[51] Int. Cl.$^6$ ........................ A01N 43/713; A61K 31/41
[52] U.S. Cl. ........................ 514/381; 548/251; 548/253; 548/254
[58] Field of Search ........................ 514/381; 548/254, 548/253, 251

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,019,152 | 5/1991 | Covey et al. | 71/92 |
| 5,120,346 | 6/1992 | Covey et al. | 71/92 |
| 5,342,954 | 8/1994 | Goto et al. | 548/251 |
| 5,344,814 | 9/1994 | Goto et al. | 504/261 |
| 5,347,009 | 9/1994 | Goto et al. | 548/251 |
| 5,347,010 | 9/1994 | Goto et al. | 548/251 |
| 5,362,704 | 11/1994 | Goto et al. | 504/134 |

FOREIGN PATENT DOCUMENTS

| | | |
|---|---|---|
| 146279 | 6/1985 | European Pat. Off. . |
| 0202929 | 11/1986 | European Pat. Off. . |
| 0578090 | 1/1994 | European Pat. Off. . |
| 0638561 | 2/1995 | European Pat. Off. . |
| 0646577 | 4/1995 | European Pat. Off. . |

*Primary Examiner*—Johann Richter
*Assistant Examiner*—Jane C. Osowecki
*Attorney, Agent, or Firm*—Sprung Horn Kramer & Woods

[57] ABSTRACT

Disclosed are herbicidal tetrazolinone derivatives, selective in paddy fields of the formula $$X_n \text{—} \underset{H}{\bigcirc} \text{—} \underset{\underset{N=\!\!=\!\!N}{|}}{N} \text{—} \overset{O}{\underset{||}{C}} \text{—} \underset{\underset{R^2}{|}}{N} \text{—} \overset{O}{\underset{||}{C}} \text{—} N \overset{R^1}{\underset{R^2}{\diagdown}} \quad (I)$$

wherein
X represents $C_{1-4}$ alkyl,
n represents 1, 2, 3 or 4,
$R^1$ and $R^2$ each independently represents $C_{1-6}$ alkyl, $C_{2-4}$ alkenyl, $C_{2-6}$ alkynyl, $C_{3-8}$ cycloalkyl, aryl which may optionally be substituted (wherein the substituent is at least one radical selected from the group consisting of halogen, $C_{1-4}$ alkyl, $C_{1-2}$ haloalkyl, $C_{1-2}$ haloalkoxy, $C_{1-2}$ haloalkylthio, acyl, nitro and cyano) or aralkyl optionally substituted by halogen or
$R^1$ and $R^2$ form, together with the N-atom to which they are bonded, a cyclic ring which may be substituted. Also, disclosed are novel intermediates useful in the preparation of the compounds of formula (I).

13 Claims, No Drawings

TETRAZOLINONES

The present invention relates to 1,4-disubstituted tetrazolinones and use thereof as herbicides. More specifically, the invention relates to novel tetrazolinones which exhibit peculiarly high activity as herbicides for paddy field, method of producing them and use thereof as herbicides for paddy field, as well as novel intermediates in the production thereof.

It has been already known that a certain kind of tetrazolinone derivatives have herbicidal activity (see: Japanese Patent Kokai Publications Sho 62-12767 and Sho 60-146879; U.S. Pat. Nos. 4,956,469, 5,019,152 and 5,003,075).

There have now been found novel tetrazolinones of the formula (I)

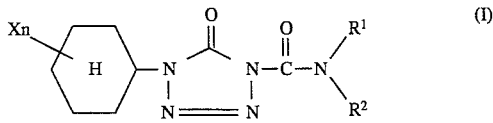

wherein

X represents $C_{1-4}$ alkyl, n represents 1, 2, 3 or 4, $R^1$ and $R^2$ each independently represents $C_{1-6}$ alkyl, $C_{2-4}$ alkenyl, $C_{2-6}$ alkynyl, $C_{3-8}$ cycloalkyl, aryl which may optionally be substituted (wherein the substituent is at least one radical selected from the group consisting of halogen, $C_{1-4}$ alkyl, $C_{1-2}$ haloalkyl, $C_{1-2}$ haloalkoxy, $C_{1-2}$ haloalkylthio, acyl, nitro and cyano) or aralkyl which may optionally be substituted by halogen or $R^1$ and $R^2$ form, together with the N-atom to which they are bonded, a cyclic ring which may optionally be substituted.

The compounds according to the invention can be produced,
when
(a) compounds of the formula (II)

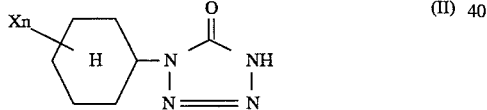

wherein X and n have the same definitions as above, are reacted with compounds of the formula (III)

wherein $R^1$ and $R^2$ have the same definitions as above, and hal represents a leaving group such as chlorine, bromine, etc. in the presence of inert solvents, and if appropriate, in the presence of an acid binder and/or a catalyst (=production method (a)).

The compounds of the formula (I) according to the invention have strong herbicidal activity. Surprisingly, the tetrazolinones of the formula (I) according to the invention exhibit extremely superior herbicidal activity as compared with those of known compounds described in the Japanese Patent Kokai Publications Sho 62-12767 and Sho 60-146879; U.S. Pat. Nos. 4,956,469, 5,019,152 and 5,003,075, and particularly they are ideal herbicidally active compounds which are selective for paddy rice, exhibiting excellent herbicidal activity against paddy field weeds while exhibiting substantially no phytotoxicity against paddy rice.

In this specification, the "alkyl" and the alkyl moiety in haloalkyl, haloalkoxy and haloalkylthio are straight-chain or branched chain, including methyl, ethyl, n-propyl, isopropyl, n-, iso-, sec- or tert-butyl, n-hexyl, n-heptyl, etc.

The "halogen" and the halogen moiety in haloalkyl, haloalkoxy and haloalkylthio include fluorine, chlorine, bromine and iodine, preferably fluorine, chlorine or bromine;

"Alkenyl" includes vinyl, 1-propenyl, allyl, 1- (2- or 3-)butenyl, etc., preferably allyl;

"Alkynyl" includes ethynyl, 1-propynyl, propargyl, 1-, 2- or 3-butynyl, 1-methyl-2-propynyl, 1,1-dimethyl-2-propynyl, etc., preferably propargyl, 1-methyl-2-propynyl or 1,1-dimethyl-2-propynyl;

"Acyl" includes all alkylcarbonyl, benzoyl, etc., preferably acetyl;

"Aryl" includes phenyl, naphthyl, etc., preferably phenyl;

"Aralkyl" represents aryl-substituted alkyl and includes benzyl, phenethyl, etc., preferably benzyl;

"Cyclic ring formed together with the N-atom" includes a 5- or 6-membered heterocyclic ring having one N-atom, or a 9- or 10-membered hydrocarbon-condensed ring thereof, and the preferred examples thereof are pyrrolidinyl, piperidinyl, indolyl, indolinyl, 1,2,3,4-tetrahydroquinolinyl, 1,2-dihydroquinolinyl, etc.

Among the tetrazolinone derivatives according to the invention, of the formula (I), preferred compounds are those in which X represents methyl or ethyl, n represents 1 or 2, $R^1$ and $R^2$ each independently represents $C_{1-4}$ alkyl, $C_{3-4}$ alkenyl, $C_{3-5}$ alkynyl, cyclopropyl, cyclopentyl, cyclohexyl, phenyl which may optionally be substituted (wherein the substituent is at least one radical selected from the group consisting of fluorine, chlorine, bromine, methyl, ethyl, n-propyl, trifluoromethyl, difluoromethoxy, trifluoromethoxy, trifluoromethylthio, acetyl, nitro and cyano) or benzyl which may optionally be substituted by chlorine, or $R^1$ and $R^2$ form, together with the N-atom to which they are bonded, a 5- or 6-membered cyclic ring which may optionally be substituted by methyl, or a benzo-condensed cyclic ring thereof.

Particularly preferred tetrazolinones of the formula (I) are those in which

X represents methyl, n represents 1 or 2, $R^1$ and $R^2$ each independently represents ethyl, n-propyl, isopropyl, n-butyl, isobutyl, sec-butyl, allyl, propargyl, 1-methyl-2-propynyl, 1,1-dimethyl-2-propynyl, cyclopropyl, cyclohexyl, phenyl which may optionally be substituted (wherein the substituent is at least one radical selected from the group consisting of fluorine, chlorine, bromine, methyl, trifluoromethyl, difluoromethoxy, trifluoromethoxy, trifluoromethylthio, acetyl, nitro and cyano), or benzyl which may optionally be substituted by chlorine, or $R^1$ and $R^2$ form, together with the N-atom to which they are bonded, 1,2,3,4-tetrahydroquinolin-1-yl or 1,2-dihydroquinolin-1-yl which may optionally be substituted by methyl.

The above production method (a) is illustrated by the following reaction scheme when, for example, 1-(2-methylcyclohexyl)-5(4H)-tetrazolinone and diethylcarbamoyl chloride are used as the starting materials.

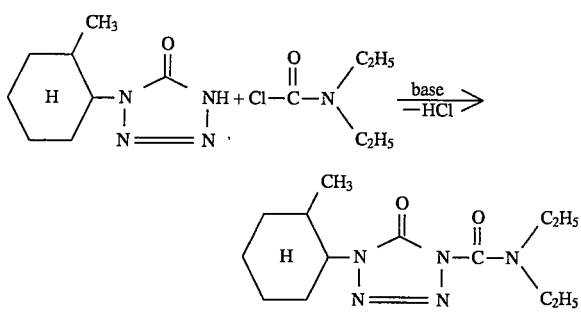

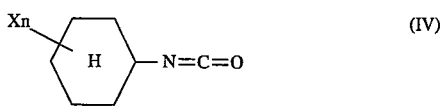

In the above production method (a), the compounds of the formula (II) as the starting materials are novel compounds and can generally be produced, for example, by any one of the following production methods (b) to (e), i.e., by a production method (b) for reacting a compound represented by the formula:

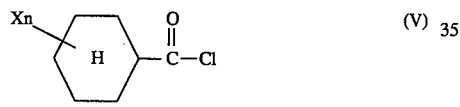

wherein X and n are defined as above, with trimethylsilyl azide in the presence of a catalytic amount of boron trifluoride ethyl etherate;

a production method (c) for reacting the compound represented by the above formula (IV) with sodium azide in a polar solvent in the presence of a catalytic amount of ammonium chloride;

a production method (d) for reacting a compound represented by the formula:

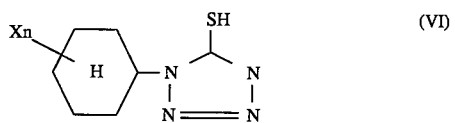

wherein X and n are defined as above, with trimethylsilyl azide; or a production method (e) for reacting a compound represented by the formula:

wherein X and n are defined as above, with a compound represented by the formula:

$$M\diagdown O\diagup \quad (VII)$$

wherein M is hydrogen atom or methyl.

In the above production methods (b) and (c), the compounds of the formula (IV) used as the starting material include isocyanates which are known in the field of organic chemistry and can be synthesized, for example, using the method described in "New Experimental Chemistry Course (Shin Jikken Kagaku Koza)" edited by Japanese Chemical Society, Vol. 14, pp 1490–1503 (Issued by Maruzen on Dec. 20, 1977).

The compounds of the formula (V) used as the starting material in the above production method (d) include acid chlorides which are known in the field of organic chemistry and can be synthesized using the method described in "New Experimental Chemistry Course (Shin Jikken Kagaku Koza)" edited by Japanese Chemical Society, Vol. 14, pp. 1104–1120 (Issued by Maruzen on Dec. 20, 1977). They can easily be obtained, for example, by reacting a cyclohexanecarboxylic acid represented by the formula:

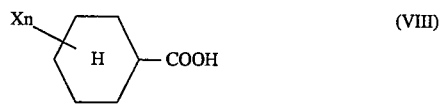

wherein X and n are defined as above, with thionyl chloride as a halogenating agent.

Further, the compounds of the above formula (VIII) can be synthesized using the method described in "New Experimental Chemistry Course (Shin Jikken Kagaku Koza)" edited by Japanese Chemical Society, Vol. 14, pp. 921–1000 (Issued by Maruzen on Dec. 20, 1977).

Furthermore, the compounds of the above formula (VIII) can also be obtained by hydrolyzing corresponding cyclohexanecarboxylic acid esters.

The compounds of the formula (VI) used as the starting material in the above production method e) can be produced, for example, using the method described in Berichte, vol. 28, pp. 74–76 (1895), i.e., by reacting a compound represented by the formula:

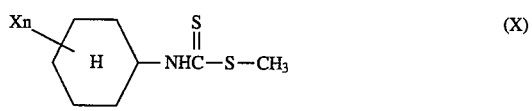

wherein X and n are defined as above, with sodium azide.

The dithiocarbamic acid ester of the above formula (X) can easily be obtained by reacting methanethiol with a compound (XI) of the formula:

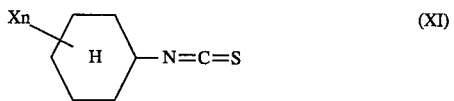

wherein X and n are defined as above, or by reacting a compound represented by the formula:

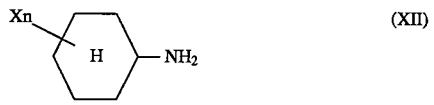

wherein X and n are defined as above, with carbon disulfide followed by further reaction with a methylating agent, for example, dimethyl sulfate or iodomethane.

The above compounds of the formula (XI) can be produced, for example, according to the method described in "New Experimental Chemistry Course (Shin Jikken Kagaku Koza)" edited by Japanese Chemical Society, Vol. 14, pp. 1503–1509 (Issued by Maruzen on Dec. 20, 1977).

Further, the compounds of the formula (XII) can be produced, for example, by the method described in "New Experimental Chemistry Course (Shin Jikken Kagaku Koza)" edited by Japanese Chemical Society, Vol. 14, pp. 1332–1399 (Issued by Maruzen on Dec. 20, 1977).

The compounds of the formula (VII) used as the starting materials in the production method (e) are known per se and exemplified by ethylene oxide or 1,2-epoxypropane.

Typical examples of the compounds of the formula (II) which are producible as mentioned above include the following compounds:

1-(1-methylcyclohexyl)-5(4H)-tetrazolinone,
1-(2-methylcyclohexyl)-5(4H)-tetrazolinone,
1-(3-methylcyclohexyl)-5(4H)-tetrazolinone, 1-(4-methylcyclohexyl)-5(4H)-tetrazolinone, 1-(2,3-dimethylcyclohexyl)-5(4H)-tetrazolinone, 1-(2,6-dimethylcyclohexyl)-5(4H)-tetrazolinone, 1-(3,5-dimethylcyclohexyl)-5(4H)-tetrazolinone, 1-(2,2-dimethylcyclohexyl)-5(4H)-tetrazolinone, 1-(4-ethylcyclohexyl)-5(4H)-tetrazolinone, 1-(3,3,5,5-tetramethylcyclohexyl)-5(4H)-tetrazolinone, and others.

The compounds of the formula (III) used as starting material in production method (a) are well known in the field of organic chemistry and examples thereof include the following compounds:

diethyl carbamoyl chloride,

N-cyclohexyl-N-ethyl carbamoyl chloride,

N-cyclopropyl-N-n-propyl carbamoyl chloride, diallyl carbamoyl chloride

N-isopropyl-N-phenyl carbamoyl chloride,

N-(2-fluorophenyl)-N-isopropyl carbamoyl chloride,

N-cyclohexyl-N-isopropyl carbamoyl chloride,

N-ethyl-N-isopropyl carbamoyl chloride,

N-(4-chlorophenyl)-N-isopropyl carbamoyl chloride,

N-isopropyl-N-(2-methylphenyl) carbamoyl chloride, 2-methyl-1,2,3,4-tetrahydroquinolin-1-yl carbonyl chloride, N-(1-methyl-2-propynyl)-N-phenyl carbamoyl chloride, N-(1,1-dimethyl-2-propynyl)-N-phenyl carbamoyl chloride, N-ethyl-N-phenyl carbamoyl chloride, 2,2-dimethyl-1,2,3,4-tetrahydroquinolin-1-yl carbonyl chloride, 2-methyl-1,2-dihydroquinolin-1-yl carbonyl chloride, 2,2-dimethyl-1,2-dihydroquinolin-1-yl carbonyl chloride, and others.

The reaction in production method (a) can be carried out in an appropriate solvent, particularly an inert organic solvent. Examples of useful solvents are aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methylethyl ether, diisopropyl ether, dibutyl ether, dioxane, dimethoxy ethane (DME), tetrahydrofuran (THF) and diethyleneglycol dimethyl ether (DGM); nitriles such as acetonitrile and propionitrile; acid amides such as dimethyl formamide (DMF), dimethyl acetamide (DMA), N-methyl pyrrolidone, 1,3-dimethyl-2-imidazolidinone and hexamethyl phosphoric triamide (HMPA); sulfones and sulfoxides such as dimethyl sulfoxide (DMSO) and sulfolan; and bases such as pyridine.

The reaction in production method (a) can be carried out in the presence of an acid binding agent and the following are mentioned as examples of acid binding agents: as inorganic bases, carbonates and bicarbonates of alkali metals such as sodium hydrogencarbonate, potassium hydrogencarbonate, sodium carbonate, potassium carbonate, etc., and, as organic bases, tertiary amines, dialkylamino anilines and pyridines such as triethylamine, 1,1,4,4-tetramethyl ethylenediamine (TMEDA), N,N-dimethyl aniline, N,N-diethyl aniline, pyridine, 4-dimethylamino pyridine (DMAP), 1,4-diazabicyclo [2,2,2]octane (DABCO), 1,8-diazabicyclo[5,4,0]undec-7-ene (DBU), and the like.

Furthermore, 4-dimethylamino pyridine can be used as the catalyst and/or the acid binding agent in order selectively to synthesize the desired compounds.

The reaction in method a) can be conducted at a temperature within a broad range but generally it is suitable to conduct it at a temperature within the range of about −30° to about 200° C. in particular about −20° to about 130° C. The reaction should preferably be conducted under normal pressure but it may be optionally conducted under elevated or reduced pressure.

Method a) can be carried out, for example, by reacting one mole of a compound of the formula (II) with 1 to 1.2 moles of a compound of the formula (III) in the presence of 1 to 1.2 moles of an acid binding agent and 4-dimethylaminopyridine in a solvent, for example, toluene, thereby to obtain the desired compounds of the formula (I).

The compounds of the formula (I) according to the invention, as shown in the test examples hereinbelow exhibit excellent herbicidal activity so that they can be used as herbicides for combating weeds, particularly as herbicides for paddy fields. Further, it has been found that herbicidal compositions having particularly high herbicidal activity can be obtained when the compounds of the formula (I) of the invention are used in combination with at least one herbicidal compound selected from the group consisting of herbicidal sulfonamides, herbicidal pyrazoles, herbicidal propionanilides, herbicidal triazines, herbicidal carbamates, herbicidal diphenyl ethers, herbicidal pyrimidines and herbicidal acid amides.

Among the above herbicidal compositions, specific examples of the herbicidal compounds usable together with the compounds of the formula (I) according to the invention are as follows:

Herbicidal sulfonamides:

N-(2-biphenylylsulfonyl)-N'-(4,6-dimethoxy-1,3,5-triazin-2-yl)urea, ethyl 5-[3-(4,6-dimethoxypyrimidin-2-yl)ureidosulfonyl]-1-methylpyrazol-4-carboxylate, methyl 2-[3-(4,6-dimethoxypyrimidin-2-yl)ureidosulfonylmethyl]benzoate, 3-(4,6-dimethoxy-1,3,5-triazin-2-yl)-1-[2-(2-methoxyethoxy)-phenylsulfonyl]urea, N-(2-chloroimidazol[1,2-a]pyridin-3-yl-sulfonyl)-N'-(4,6-dimethoxy-2-pyrimidyl)urea, N'-(4,6-dimethoxypyrimidin-2-yl)-N''-(4-methylphenylsulfonylamino)-N'''-(4-ethoxycarbonyl-1-methylpyrazol-5-yl-sulfonyl-guanidine, N-(2-cyclopropylcarbonylphenylsulfamoyl)-N'-(4,6-dimethoxypyrimidin-2-yl)urea, etc.

These compounds are known per se and disclosed in Japanese Patent Kokoku Publication Sho 59-481; Japanese Patent Kokai Publications Sho 57-112379, Sho 57-56452, Sho 59-122488, Hei 1-38091, Hei 1-70475, etc.

Herbicidal pyrazoles:

4-(2,4-dichlorobenzoyl)-1,3-dimethylpyrazol-5-yl p-toluene sulfonate,

2-[4-(2,4-dichlorobenzoyl)-1,3-dimethylpyrazol-5-yl]acetophenone,

2-[4-(2,4-dichloro-m-toluoyl)-1,3-dimethylpyrazol-5-yloxy]-4-methylacetophenone, etc.

Herbicidal propionanilides:

2-(β-naphthyloxy)propionanilide, (RS)-2-(2,4-dichloro-m-tolyloxy)propionanilide, etc.

Herbicidal triazines:

2,4-bis(ethylamino)-6-(methylamino)-1,3,5-triazine, 2-ethylamino-4-(1,2-dimethylpropylamino)-6-methylthio-1,3,5-triazine, etc.

Herbicidal carbamates:
  S-p-chlorobenzyl diethylthiocarbamate,
  S-1-methyl-1-phenylethyl piperidin-1-carbothioate,
  S-benzyl 1,2-dimethylpropyl(ethyl)thiocarbamate, etc.
Herbicidal diphenyl ethers:
  2,4,6-trichlorophenyl-4'-nitrophenyl ether,
  2,4-dichlorophenyl-3'-methoxy-4'-nitrophenyl ether, etc.
Herbicidal pyrimidines:
  methyl 2-[(4,6-dimethoxy-2-pyrimidinyl)oxy]-6-[1-(methoxyimino)ethyl]-benzoate, etc.
Herbicidal acid amides:
  (RS)-2-bromo-N-(α,α-dimethylbenzyl)-3,3-dimethylbutyramide, etc.

The above herbicidal compounds are described, for instance, in Pesticides Manual, 1991, issued by the British Crop Protect Council.

Further, the above herbicidal pyrimidines are described in BCPC Weeds, 1993, Brighton, Nov. 22–25th, 1993, Vol. 1, Ref. 2-b.

In the above herbicidal compositions, the weight ratio of each effective component can be varied over a relatively wide range, but, in general, it may suitably be set up within the following range: That is per part by weight of the compounds of the formula (I);

0.01–2 parts by weight, preferably 0.05–1 part by weight of herbicidal sulfonamides,
  2.5–35 parts by weight, preferably 3–15 parts by weight of herbicidal pyrazoles,
  0.6–50 parts by weight, preferably 2.0–28 parts by weight of herbicidal propionanilides,
  0.06–10 parts by weight, preferably 0.15–6 parts by weight of herbicidal triazines,
  3–15 parts by weight, preferably 5–10 parts by weight of herbicidal carbamates,
  5–35 parts by weight, preferably 7–15 parts by weight of herbicidal diphenyl ethers,
  0.01–2 parts by weight, preferably 0.1–1 part by weight of herbicidal pyrimidines, and
  3.5–25 parts by weight, preferably 4.0–10 parts by weight of herbicidal acid amides.

The above herbicidal compositions exhibit strong herbicidal activity against various weeds. Therefore, the compositions can be used as herbicidal compositions and particularly exhibit excellent effect as a herbicide which is selective for paddy rice.

The herbicidal compounds and above herbicide compositions according to the present invention can be used to combat paddy field weeds, for example, of the following species:
Dicotyledon weeds of the genera:
  Polygonum, Rorippa, Rotala, Lindernia, Bidens, Dopatrium, Eclipta, Elatine, Gratiola, Vandellia, Ludwigia, Oenanthe, Ranunculus and Deinostema.
Monocotyledon weeds of the genera:
  Echinochloa, Panicum, Poa, Cyperus, Monochoria, Fimbristylis, Sagittaria, Eleocharis, Scirpus, Alisma, Aneilema, Blyxa, Eriocaulon and Potamogeton.

More specifically, they can be used, for example, for combating the following paddy field weeds, scientific name (plant name):
Dicotyledon weeds
*Rotala indica* Koehne (Indian toothcup)
Lindernia Procumbens Philcox (common false impernel)
*Ludwigia prostrata* Roxburgh (false loosestrife)
*Potamogeton distinctus* A. Benn (bog pondweed)
*Elatine triandra* Schk (long stemmed water wort)
*Oenanthe javanica* (Blume) DC. (dropwort)
Monocotyledon weeds:
*Echinochloa oryzicola* vasing (barnyardgrass)
*Monochoria vaginalis* Presl (monochoria)
*Eleocharis acicularis* L. (cow hairs)
*Eleocharis Kuroguwai* Ohwi (water chestnut)
*Cyperus difformis* L. (smallflower)
*Cyperus serotinus* Rottboel (water nutgrass)
*Sagittaria pygmaea* Miq (Japanese ribbon wapato)
*Alisma canaliculatum* A. Br. et Bouche (narrow-leaved arrowhead)
*Scirpus juncoides* Roxburgh (bulrush).

However, use of the herbicidal compounds and the above herbicidal compositions of the invention are in no way restricted to these weeds and equally extend to other paddy field weeds.

The herbicides and the above herbicidal compositions of the invention can be used in the form of the customary formulations, such as solutions, emulsions, wettable powders, suspensions, powders, soluble powders, granules, tablets, suspension-emulsion concentrates, very fine capsules in polymeric substances, natural and synthetic materials impregnated with the active compounds, etc.

Those formulations are prepared in a manner known per se, for example, by mixing the active compounds with extenders, that is liquid solvents and/or solid carriers, optionally with the use of surface-active agents, that is emulsifying agents and/or dispersing agents and/or foam-forming agents.

As liquid solvents, there are suitable in the main: aromatic hydrocarbons, such as xylene, toluene or alkyl naphthalenes; chlorinated aromatic hydrocarbons and chlorinated aliphatic hydrocarbons, such as chlorobenzenes, chloroethylenes or methylene chloride; aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone; strongly polar solvents, such as dimethylformamide and dimethylsulfoxide; as well as water. In the case of the use of water as an extender, organic solvents can be used as auxiliary solvents if necessary.

As solid carriers there are suitable: for example, ammonium salts and ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulfonates, alkylsulfates, arylsulfonates as well as albumin hydrolysis products.

As dispersing agents there are suitable: for example, lignin-sulphite waste liquors and methylcellulose, etc.

Adhesives may also be used optionally in formulations such as powders, granules, natural and synthetic materials impregnated with active compound or emulsions, and the following are mentioned as examples of useful adhesives: for example, carboxymethylcellulose and natural and synthetic polymers such as gum arabic, polyvinyl alcohol and polyvinyl acetate, as well as natural products, such as cephalins and lecithins, synthetic phospholipids. Further, as additives, mineral and vegetable oils can be incorporated.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of metals, for example, iron, manganese, boron, copper, molybdenum, cobalt and zinc.

The formulations can contain, in general, 0.1 to 95% by weight, preferably 0.5 to 90% by weight, of the active compounds.

The active compounds in the herbicidal compounds and in the above herbicidal compositions according to the invention can be used for combating undesired weeds, as they are or in the form of such formulations. The formulations may be either prepared in advance in the form of a final formulation or prepared by tank-mixing immediately before use. Further, the herbicides and the above herbicidal compositions according to the invention may contain other known active compounds, for example, active compounds which are usually used in paddy fields, such as fungicides, insecticides, plant growth regulators, plant nutrients, soil-improving agents, phytotoxicity mitigators and other herbicides. In a preferred embodiment, 1–200 parts by weight, preferably 2–100 parts by weight of, for example, 1-(α,α-dimethylbenzyl)-3-p-tolylurea as a phytotoxicity mitigator or of a herbicidal sulfonamide may be added to the herbicidal composition per part by weight of the above herbicidal composition.

The active compounds can be used as such, in the form of their formulations or in the use forms prepared therefrom by further dilution, such as ready-to-use solutions, emulsions, suspensions, powders, wettable powders and granules. They are used in the customary manner, for example by watering, spraying, atomizing, scattering or dusting.

The herbicides and the above herbicidal compositions according to the invention can be applied either before or after emergence of the plants.

In the herbicides of the invention, the amount of the active compound applied can be varied within a range depending on the nature of the desired effect, but in general, the amount can be exemplified by about 0.01 kg/ha to about 10 kg/ha, preferably about 0.1 kg/ha to about 2 kg/ha, of active compound of the invention.

Further, in the above herbicidal composition, the amount of the composition applied can be varied within a wide range. The application amount is, in general, within a range of 0.1 kg/ha to 5 kg/ha, preferably between 0.2 kg/ha to 3 kg/ha, as the total amounts of effective components.

The following examples illustrate the compounds of the invention and the use thereof as a herbicide, but they should not be regarded as limiting the invention in any way.

EXAMPLES

Production Examples:

Example 1

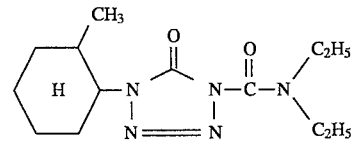

1-(2-methylcyclohexyl)-5(4H)-tetrazolinone (2 g), 4-dimethylaminopyridine (1.6 g) and diethylcarbamoyl chloride (1.7 g) were suspended in toluene (70 ml) and the mixture was stirred at 50°–55° C. for 5–6 hours. After cooling, the organic layer was washed successively with water, 1% hydrochloric acid, water, a saturated aqueous sodium hydrogen carbonate solution and water. After drying the organic layer over anhydrous sodium sulfate, the solvent was distilled off under reduced pressure, and the residue was purified by column chromatography (eluant: chloroform) to obtain the desired 1-(2-methylcyclohexyl)-4-(diethylcarbamoyl)-5(4H)-tetrazolinone (2.6 g). $N_D^{20}$ 1.4992

Further tetrazolinone derivatives producible by process (a) are shown in Table 1, together with the compound of the above Example 1 (as Compound No. 27):

TABLE 1

(I)

| Compound No. | Xn | R¹ | —(N)— | R² | mp. °C./$n_D^{20}$ |
|---|---|---|---|---|---|
| 1 | 1-CH₃ | C₂H₅ | | C₂H₅ | |
| 2 | 1-CH₃ | C₂H₅ | | ⟨hexyl⟩ | |
| 3 | 1-CH₃ | C₃H₇-n | | ▵ | |
| 4 | 1-CH₃ | CH₂CH=CH₂ | | CH₂CH=CH₂ | |

TABLE 1-continued $$\underset{H}{X_n-}\text{cyclohexyl}-\underset{\underset{N}{\overset{\|}{N}}}{N}-\underset{\underset{\|}{N}}{\overset{O}{\overset{\|}{C}}}-\underset{\underset{(N)}{\mid}}{N}-\underset{\underset{}{\overset{O}{\overset{\|}{C}}}}{}-N\underset{R^2}{\overset{R^1}{<}} \quad (I)$$

| Compound No. | Xn | R¹ | —(N)— | R² | mp. °C./$n_D^{20}$ |
|---|---|---|---|---|---|
| 5 | 1-CH₃ | C₃H₇-iso | | phenyl | 1.5192 |
| 6 | 1-CH₃ | C₃H₇-iso | | 2-F-phenyl | |
| 7 | 1-CH₃ | C₃H₇-iso | | 4-F-phenyl | |
| 8 | 1-CH₃ | C₃H₇-iso | | 4-Cl-phenyl | |
| 9 | 1-CH₃ | C₃H₇-iso | | 3,5-Cl₂-phenyl | |
| 10 | 1-CH₃ | C₃H₇-iso | | 4-Br-phenyl | |
| 11 | 1-CH₃ | C₃H₇-iso | | 3-CF₃-phenyl | |
| 12 | 1-CH₃ | C₃H₇-iso | | 4-CH₃-phenyl | |
| 13 | 1-CH₃ | C₃H₇-iso | | 3-COCH₃-phenyl | |
| 14 | 1-CH₃ | | 2-methylpyrrolidin-1-yl | | |
| 15 | 1-CH₃ | | 2-methylindolin-1-yl | | |

TABLE 1-continued
(I)
| Compound No. | Xn | R¹ | R² | mp. °C./$n_D^{20}$ |
|---|---|---|---|---|
| 16 | 1-CH$_3$ | CH$_2$C≡CH | 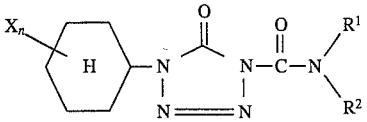 | |
| 17 | 1-CH$_3$ | CH(CH$_3$)$_2$C≡CH | 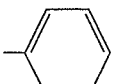 | |
| 18 | 1-CH$_3$ | C(CH$_3$)$_2$C≡CH | 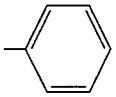 | |
| 19 | 1-CH$_3$ | C$_2$H$_5$ | 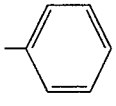 | |
| 20 | 1-CH$_3$ | C$_3$H$_7$-n | 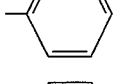 | |
| 21 | 1-CH$_3$ | C$_4$H$_9$-n | 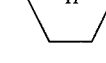 | |
| 22 | 1-CH$_3$ | C$_4$H$_9$-sec | 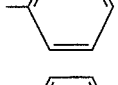 | |
| 23 | 1-CH$_3$ | C$_4$H$_9$-iso | 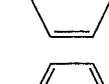 | |
| 24 | 1-CH$_3$ | CH(CH$_3$)C≡CH |  | |
| 25 | 1-CH$_3$ | C(CH$_3$)$_2$C≡CH | 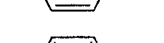 | |
| 26 | 1-CH$_3$ | C$_3$H$_7$-iso |  | |
| 27 | 2-CH$_3$ | C$_2$H$_5$ | C$_2$H$_5$ | 1.4992 |
| 28 | 2-CH$_3$ | C$_2$H$_5$ | 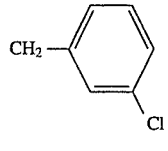 | 1.5011 |

TABLE 1-continued
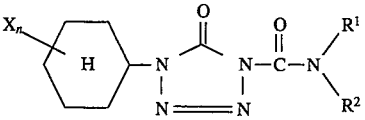
(I)
| Compound No. | Xn | R¹ | —(N)— | R² | mp. °C./$n_D^{20}$ |
|---|---|---|---|---|---|
| 29 | 2-CH₃ | C₃H₇-iso | | 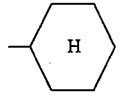 | 1.4975 |
| 30 | 2-CH₃ | C₃H₇-iso | | C₂H₅ | 1.4931 |
| 31 | 2-CH₃ | C₃H₇-iso | | 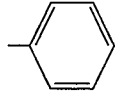 | 1.5292 |
| 32 | 2-CH₃ | C₃H₇-iso | | 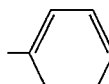 | 1.5311 |
| 33 | 2-CH₃ | C₃H₇-iso | | 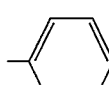 | |
| 34 | 2-CH₃ | C₃H₇-iso | | 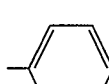 | 1.5163 |
| 35 | 2-CH₃ | C₃H₇-iso | |  | |
| 36 | 2-CH₃ | C₃H₇-iso | | 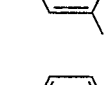 | |
| 37 | 2-CH₃ | C₃H₇-iso | | 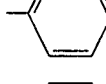 | |
| 38 | 2-CH₃ | 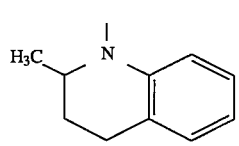 | | | 1.5422 |
| 39 | 2-CH₃ | CH(CH₃)C≡CH | | 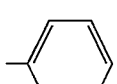 | |
| 40 | 2-CH₃ | C(CH₃)₂C≡CH | | 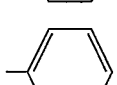 | 99.5–101.5 |
| 41 | 2-CH₃ | CH₃ | | 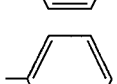 | |

TABLE 1-continued

Structure (I):
X$_n$-C$_6$H$_{10}$(H)-N-N=N-N(-)-C(=O)-N-C(=O)-NR$^1$R$^2$ tetrazine with —(N)— substituent

| Compound No. | Xn | R$^1$ | —(N)— | R$^2$ | mp. °C./n$_D^{20}$ |
|---|---|---|---|---|---|
| 42 | 2-CH$_3$ | C$_2$H$_5$ | | phenyl | 1.5234 |
| 43 | 2-CH$_3$ | C$_3$H$_7$-n | | phenyl | |
| 44 | 2-CH$_3$ | C$_4$H$_9$-sec | | phenyl | 1.5211 |
| 45 | 2-CH$_3$ | CH(CH$_3$)C≡CH | | 4-Cl-phenyl | |
| 46 | 2-CH | CH(CH$_3$)C≡CH | | 4-NO$_2$-phenyl | |
| 47 | 2-CH$_3$ | C(CH$_3$)$_2$C≡CH | | 4-Cl-phenyl | |
| 48 | 2-CH$_3$ | C(CH$_3$)$_2$C≡CH | | 4-F-phenyl | |
| 49 | 2-CH$_3$ | C(CH$_3$)$_2$C≡CH | | CH$_2$-phenyl | |
| 50 | 3-CH$_3$ | C$_2$H$_5$ | | C$_2$H$_5$ | |
| 51 | 3-CH$_3$ | C$_2$H$_5$ | | cyclohexyl (H) | |
| 52 | 3-CH$_3$ | C$_2$H$_5$ | | C$_3$H$_7$-iso | |
| 53 | 3-CH$_3$ | CH$_2$CH=CH$_2$ | | CH$_2$CH=CH$_2$ | |
| 54 | 3-CH$_3$ | C$_2$H$_5$ | | phenyl | |
| 55 | 3-CH$_3$ | C$_3$H$_7$-n | | phenyl | |
| 56 | 3-CH$_3$ | C$_3$H$_7$-iso | | phenyl | 1.5230 |

TABLE 1-continued
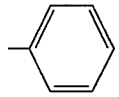
(I)
| Compound No. | Xn | R¹ | —(N)— | R² | mp. °C./$n_D^{20}$ |
|---|---|---|---|---|---|
| 57 | 3-CH₃ | C₄H₉-sec | | 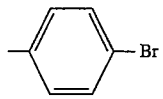 | |
| 58 | 3-CH₃ | C₃H₇-iso | | 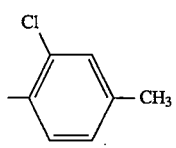 Br | |
| 59 | 3-CH₃ | C₃H₇-iso | | 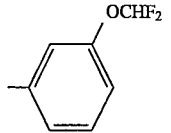 Cl, CH₃ | |
| 60 | 3-CH₃ | C₃H₇-iso | | 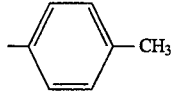 OCHF₂ | |
| 61 | 3-CH₃ | C₃H₇-iso | | 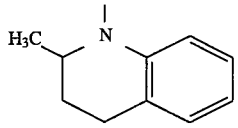 CH₃ | |
| 62 | 3-CH₃ | | 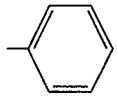 | | |
| 63 | 3-CH₃ | C(CH₃)₂C≡CH | | 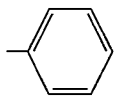 | |
| 64 | 3-CH₃ | CH(CH₃)C≡CH | | 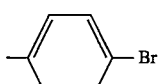 | |
| 65 | 3-CH₃ | CH(CH₃)C≡CH | | 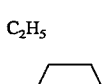 Br | |
| 66 | 4-CH₃ | C₂H₅ | | C₂H₅ | |
| 67 | 4-CH₃ | C₂H₅ | | 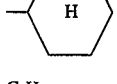 | |
| 68 | 4-CH₃ | C₃H₇-n | | C₃H₇-n | |
| 69 | 4-CH₃ | C₃H₇-n | |  | |
| 70 | 4-CH₃ | C₃H₇-n | | 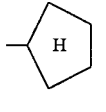 | |

TABLE 1-continued

Structure (I):

X_n-cyclohexyl-N(H)-N(-)-C(=O)-N(-(N)-)-N=N-C(=O)-N(R^1)(R^2)

| Compound No. | $X_n$ | $R^1$ | $R^2$ | mp. °C./$n_D^{20}$ |
|---|---|---|---|---|
| 71 | 4-CH$_3$ | C$_3$H$_7$-iso | 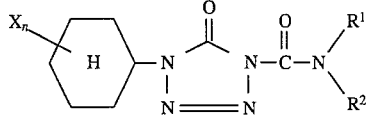 phenyl | 1.5276 |
| 72 | 4-CH$_3$ | C$_3$H$_7$-iso | 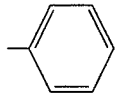 2-F-phenyl | |
| 73 | 4-CH$_3$ | C$_3$H$_7$-iso | 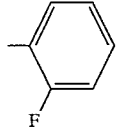 4-F-phenyl | |
| 74 | 4-CH$_3$ | C$_3$H$_7$-iso | 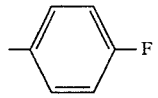 4-CF$_3$-phenyl | |
| 75 | 4-CH$_3$ | C$_3$H$_7$-iso | 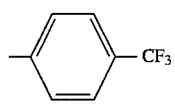 CH$_2$-phenyl | |
| 76 | 4-CH$_3$ | C(CH$_3$)$_2$C≡CH | 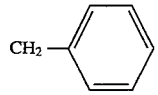 phenyl | |
| 77 | 4-CH$_3$ | C(CH$_3$)$_2$C≡CH | 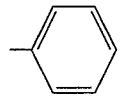 4-Br-phenyl | |
| 78 | 4-CH$_3$ | CH(CH$_3$)C≡CH | 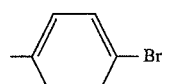 phenyl | |
| 79 | 2,3-(CH$_3$)$_2$ | C$_2$H$_5$ | C$_2$H$_5$ | |
| 80 | 2,3-(CH$_3$)$_2$ | C$_2$H$_5$ | 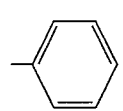 cyclohexyl | 1.5039 |
| 81 | 2,3-(CH$_3$)$_2$ | C$_3$H$_7$-iso | 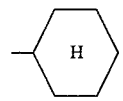 phenyl | 1.5200 |
| 82 | 2,3-(CH$_3$)$_2$ | C$_3$H$_7$-iso | 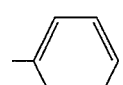 4-Cl-phenyl | 1.5261 |
| 83 | 2,3-(CH$_3$)$_2$ | C$_3$H$_7$-iso | 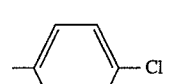 4-F-phenyl | 1.5119 |

TABLE 1-continued

Structure (I):

X_n-C6H10-N(H)-N(C=O)-N=N with —(N)— branch, connected to C(=O)-N(R¹)(R²)

| Compound No. | Xn | R¹ | —(N)— | R² | mp. °C./$n_D^{20}$ |
|---|---|---|---|---|---|
| 84 | 2,3-(CH₃)₂ | C₃H₇-iso | | 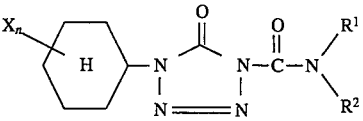 4-CH₃-C₆H₄- | 1.5195 |
| 85 | 2,3-(CH₃)₂ | C₃H₇-iso | | 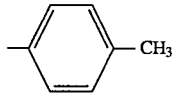 3,5-Cl₂-C₆H₃- | |
| 86 | 2,3-(CH₃)₂ | C₃H₇-iso | | 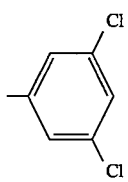 4-CN-C₆H₄- | |
| 87 | 2,3-(CH₃)₂ | | 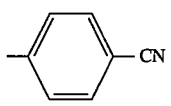 2-methyl-1,2,3,4-tetrahydroquinolin-1-yl | | |
| 88 | 2,3-(CH₃)₂ | CH(CH₃)C≡CH | | 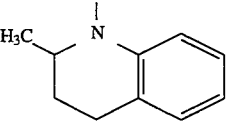 C₆H₅- | |
| 89 | 2,3-(CH₃)₂ | C(CH₃)₂C≡CH | | 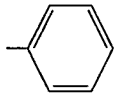 C₆H₅- | 1.5154 |
| 90 | 2,3-(CH₃)₂ | C(CH₃)₂C≡CH | | 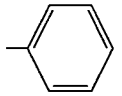 4-Cl-C₆H₄- | |
| 91 | 2,3-(CH₃)₂ | C(CH₃)₂C≡CH | | 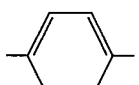 4-F-C₆H₄- | |
| 92 | 2,3-(CH₃)₂ | C₂H₅ | | 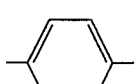 C₆H₅- | |
| 93 | 2,3-(CH₃)₂ | C₃H₇-n | | 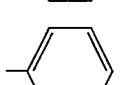 C₆H₅- | |
| 94 | 2,3-(CH₃)₂ | C₄H₉-sec | | 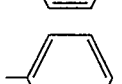 C₆H₅- | 1.5452 |
| 95 | 2,3-(CH₃)₂ | C₃H₇-iso | |  3-F-C₆H₄- | |

TABLE 1-continued
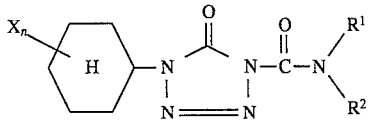
(I)
| Compound No. | Xn | R¹ | —(N)— | R² | mp. °C./$n_D^{20}$ |
|---|---|---|---|---|---|
| 96 | 2,3-(CH$_3$)$_2$ | C$_3$H$_7$-iso | | 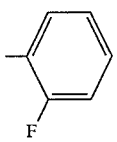 | |
| 97 | 2,3-(CH$_3$)$_2$ | C$_3$H$_7$-iso | | 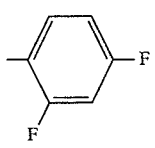 | |
| 98 | 2,6-(CH$_3$)$_2$ | C$_2$H$_5$ | | C$_2$H$_5$ | |
| 99 | 2,6-(CH$_3$)$_2$ | C$_2$H$_5$ | | 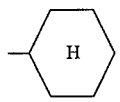 | |
| 100 | 2,6-(CH$_3$)$_2$ | C$_3$H$_7$-iso | | 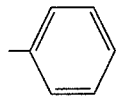 | 75–79 |
| 101 | 2,6-(CH$_3$)$_2$ | C$_3$H$_7$-iso | |  | 1.5292 |
| 102 | 2,6-(CH$_3$)$_2$ | C$_3$H$_7$-iso | | 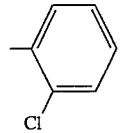 | |
| 03 | 2,6-(CH$_3$)$_2$ | C$_3$H$_7$-iso | | 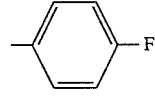 | |
| 104 | 2,6-(CH$_3$)$_2$ | C$_3$H$_7$-iso | | 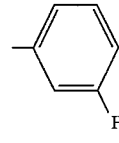 | |
| 105 | 2,6-(CH$_3$)$_2$ | C$_3$H$_7$-iso | | 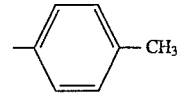 | 90–94 |
| 106 | 2,6-(CH$_3$)$_2$ | CH(CH$_3$)C≡CH | | 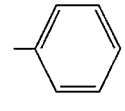 | |
| 107 | 2,6-(CH$_3$)$_2$ | C(CH$_3$)$_2$C≡CH | | 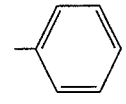 | |

TABLE 1-continued (I)

| Compound No. | Xn | R¹ | —(N)— | R² | mp. °C./$n_D^{20}$ |
|---|---|---|---|---|---|
| 108 | 2,6-($CH_3$)$_2$ | C($CH_3$)$_2$C≡CH | | 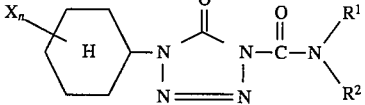 4-Br-C₆H₄ | |
| 109 | 2,6-($CH_3$)$_2$ | $CH_2CH=CH_2$ | | 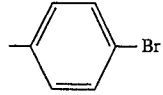 C₆H₅ | |
| 110 | 2,6-($CH_3$)$_2$ | | 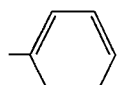 2-methyl-1,2,3,4-tetrahydroquinolinyl | | |
| 111 | 3,5-($CH_3$)$_2$ | $C_2H_5$ | | $C_2H_5$ | |
| 112 | 3,5-($CH_3$)$_2$ | $C_2H_5$ | | 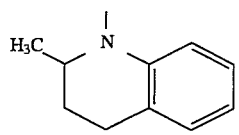 cyclohexyl | |
| 113 | 3,5-($CH_3$)$_2$ | $C_3H_7$-iso | | 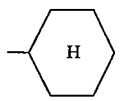 C₆H₅ | |
| 114 | 3,5-($CH_3$)$_2$ | $C_3H_7$-iso | | 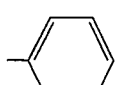 4-Cl-C₆H₄ | |
| 115 | 3,5-($CH_3$)$_2$ | $C_3H_7$-iso | | 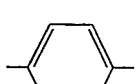 4-F-C₆H₄ | |
| 116 | 3,5-($CH_3$)$_2$ | $C_3H_7$-iso | | 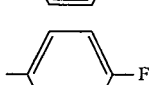 4-CH₃-C₆H₄ | |
| 117 | 3,5-($CH_3$)$_2$ | $C_3H_7$-iso | |  3,5-(CH₃)₂-C₆H₃ | |
| 118 | 3,5-($CH_3$)$_2$ | $C_3H_7$-iso | |  4-Br-C₆H₄ | |
| 119 | 3,5-($CH_3$)$_2$ | CH($CH_3$)C≡CH | | 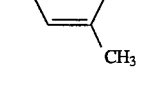 C₆H₅ | |
| 120 | 3,5-($CH_3$)$_2$ | C($CH_3$)$_2$C≡CH | | 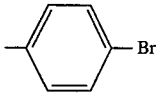 C₆H₅ | |

TABLE 1-continued
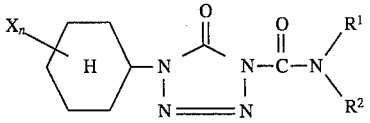
(I)
| Compound No. | Xn | R¹ | —(N)— | R² | mp. °C./$n_D^{20}$ |
|---|---|---|---|---|---|
| 121 | 3,5-(CH₃)₂ | C(CH₃)₂C≡CH | | 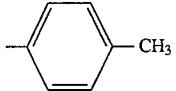 | |
| 122 | 3,5-(CH₃)₂ | | 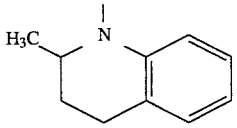 | | |
| 123 | 3,5-(CH₃)₂ | C₄H₉-sec | | 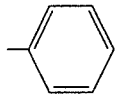 | |
| 124 | 3,5-(CH₃)₂ | C₂H₅ | | 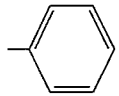 | |
| 125 | 2,2-(CH₃)₂ | C₃H₇-iso | | 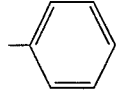 | |
| 126 | 4-C₂H₅ | C₃H₇-iso | | 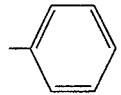 | |
| 127 | 3,3,5,5-(CH₃)₄ | C₃H₇-iso | | 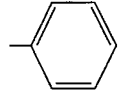 | |
| 128 | 2,2-(CH₃)₂ | C₃H₇-iso | |  | |
| 129 | 2,2-(CH₃)₂ | C₃H₇-iso | | 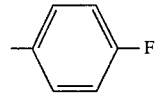 | |
| 130 | 2,2-(CH₃)₂ | C₃H₇-iso | | 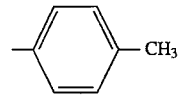 | |
| 131 | 2,2-(CH₃)₂ | C(CH₃)C≡CH | | 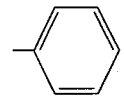 | |
| 132 | 2,2-(CH₃)₂ | C(CH₃)₂C≡CH | | 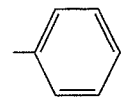 | |

TABLE 1-continued

Structure (I): Xn-cyclohexyl-N(H)-N-C(=O)-N-C(=O)-N(R¹)(R²), with tetrazole ring containing —(N)— substituent

| Compound No. | Xn | R¹ | —(N)— | R² | mp. °C./$n_D^{20}$ |
|---|---|---|---|---|---|
| 133 | 2-CH$_3$ | | | 2,2-dimethyl-1,2,3,4-tetrahydroquinolin-1-yl | |
| 134 | 2-CH$_3$ | | | 2,2-dimethyl-2H-quinolin-1-yl | |
| 135 | 2,6-(CH$_3$)$_2$ | C$_3$H$_7$-iso | | 3-methylphenyl | |
| 136 | 2,6-(CH$_3$)$_2$ | | | 2,2-dimethyl-1,2,3,4-tetrahydroquinolin-1-yl | |
| 137 | 2,6-(CH$_3$)$_2$ | | | 2,2-dimethyl-2H-quinolin-1-yl | |
| 138 | 2,6-(CH$_3$)$_2$ | | | 2-methyl-6-fluoro-1,2,3,4-tetrahydroquinolin-1-yl | |
| 139 | 2,5-(CH$_3$)$_2$ | C$_2$H$_5$ | | C$_2$H$_5$ | |
| 140 | 2,5-(CH$_3$)$_2$ | C$_2$H$_5$ | | cyclohexyl | |
| 141 | 2,5-(CH$_3$)$_2$ | C$_3$H$_7$-iso | | phenyl | |
| 142 | 2,5-(CH$_3$)$_2$ | C$_3$H$_7$-iso | | 4-fluorophenyl | |
| 143 | 2,5-(CH$_3$)$_2$ | C$_3$H$_7$-iso | | 4-methylphenyl | |
| 144 | 2,5-(CH$_3$)$_2$ | C(CH$_3$)$_2$C≡CH | | phenyl | |

TABLE 1-continued $$\text{(I)}\quad X_n\text{—}\underset{H}{\bigcirc}\text{—}\underset{\underset{N=\!=\!=N}{|}}{N}\text{—}\overset{O}{\underset{}{C}}\text{—}\underset{\underset{-(N)-}{|}}{N}\text{—}\overset{O}{\underset{}{C}}\text{—}N\overset{R^1}{\underset{R^2}{\diagdown}}$$

| Compound No. | Xn | R¹ | —(N)— | R² | mp. °C./$n_D^{20}$ |
|---|---|---|---|---|---|
| 145 | 2,5-(CH₃)₂ | | H₃C,H₃C-substituted tetrahydroquinoline | | |
| 146 | 2-CH₃ | | H₃C-substituted indole | | |

Example 2

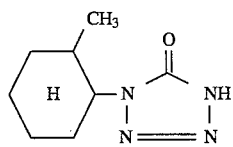

2-Methylcyclohexyl isocyanate (10 g), trimethylsilyl azide (12.4 g) and a catalytic amount of boron trifluoride ethyl etherate were mixed and the mixture was heated for 40 hours with refluxing. The excess trimethylsilyl azide was distilled off under reduced pressure and methanol was added to the residue. Then, methanol was distilled off under reduced pressure and the residue was purified by column chromatography (eluant: ethanol/chloroform=4/100) to obtain the desired 1-(2-methylcyclohexyl)-5(4H)-tetrazolinone (10.2 g). mp. 109°–113° C.

Example 3

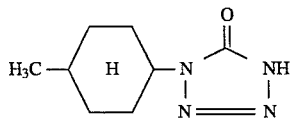

4-methylcyclohexylcarbonyl chloride (10 g), trimethylsilyl azide (20.7 g) and a catalytic amount of boron trifluoride ethyl etherate were mixed and the mixture was heated for 48 hours with refluxing. The excess trimethylsilyl azide was distilled off under reduced pressure and methanol was added to the residue. Then, methanol was distilled off under reduced pressure and the residue was purified by column chromatography (eluant: ethanol/chloroform=4/100) to obtain the desired 1-(4-methylcyclohexyl)-5(4H)-tetrazolinone (9.5 g). mp. 91°–95° C.

Further compounds of formula (II) producible by any of the above-mentioned production methods (b) and (e) are shown in Table 2, together with the compounds of the above Examples 2 and 3 (as Compounds No. II.2 and No. II.4, respectively).

TABLE 2

$$\text{(II)}\quad X_n\text{—}\underset{H}{\bigcirc}\text{—}\underset{\underset{N=\!=\!=N}{|}}{N}\text{—}\overset{O}{\underset{}{C}}\text{—}NH$$

| Compound No. | Xn | mp. °C./$n_D^{20}$ |
|---|---|---|
| II.1 | 1-CH₃ | 1.4926 |
| II.2 | 2-CH₃ | 109–113 |
| II.3 | 3-CH₃ | 1.5081 |
| II.4 | 4-CH₃ | 91–95 |
| II.5 | 2,3-(CH₃)₂ | 84–87.5 |
| II.6 | 2,6-(CH₃)₂ | 145–146.5 |
| II.7 | 2,2-(CH₃)₂ | |
| II.8 | 4-C₂H₅ | |
| II.9 | 3,5-(CH₃)₂ | |
| II.10 | 3,3,5,5-(CH₃)₄ | |
| II.11 | 2,5-(CH₃)₂ | 106–109.5 |

Biological Test Examples

Comparative Compounds

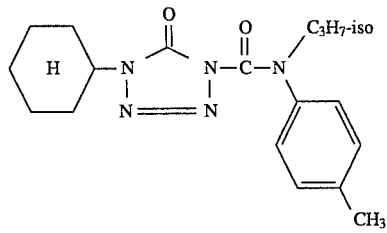

C-1

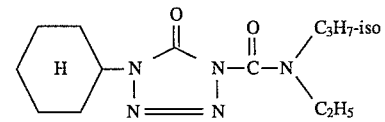

C-2

Example 4 (Biological Test)

Test of herbicidal effect on paddy field weeds
Preparation of testing chemicals
carrier: acetone, 5 parts by weight
emulsifier: benzyloxy polyglycol ether, 1 part by weight One part of an active compound and the above amounts of carrier and emulsifier are mixed to obtain a formulation of the active substance as an emulsion. A prescribed amount of this formulation is diluted with water to prepare testing chemicals.

Testing procedure

In the greenhouse, 3 seedlings of paddy rice (cultivar: Nipponbare) of 2.5 leafstage (15 cm tall) were transplanted in two places in a 1/2000 are large pot (25×25×9 cm) filled with paddy field soil. Then seeds of barnyardgrass, smallflower umbrellaplant, monochoria, broad-leaved weeds (common falsepimpernel, Indian toothcup, long stemmed water wort, *Ammannia multiflora* Roxb., *Dopatrium junceum* Hammilt), bulrush were sowed, and water was poured on the soil to a depth of about 2–3 cm. The testing chemicals prepared according to the above preparation method were applied to the surface of the water 5 days after the transplanting of the paddy rice.

The herbicidal effect and the degree of phytotoxicity against crop plants were examined on the day after 3 weeks from the application during which period the water depth of 3 cm was maintained.

The herbicidal effect was rated as 100% in the case of complete death and as 0% in the case where no herbicidal effect was observed. The results are indicated in the following Table 3.

TABLE 3

| compound No. Table 1) | rate/ concentration (kg/ha) | herbicidal effect | | | | | phytotoxicity rice |
|---|---|---|---|---|---|---|---|
| | | barnyard grass | smallflower umbrella plant | bulrush | monochoria | broadleaved weeds | |
| 31 | 0.25 | 100 | 100 | 90 | 100 | 90 | 0 |
| 32 | 0.25 | 100 | 100 | 100 | 100 | 90 | 0 |
| 38 | 0.25 | 100 | 100 | 90 | 100 | 90 | 0 |
| 81 | 0.25 | 100 | 100 | 90 | 100 | 90 | 0 |
| 83 | 0.25 | 100 | 100 | 90 | 100 | 90 | 0 |
| Comparative: | | | | | | | |
| C-1 | 0.25 | 80 | 90 | 70 | 90 | 80 | 10 |
| C-2 | 0.25 | 100 | 100 | 90 | 100 | 90 | 30 |

Formulation Example 1

Water was added to a mixture of 1.25 parts by weight of Compound No. 31, 30 parts by weight of bentonite, 66.75 parts by weight of talc and 2 parts by weight of lignin sulfonate salt, and the mixture was thoroughly kneaded followed by granulating and drying to obtain granules.

It will be appreciated that the instant specification and claims are set forth by way of illustration and not limitation, and that various modifications and changes may be made without departing from the spirit and scope of the present invention.

We claim:

1. A tetrazolinone of the formula $$\text{(I)}$$

wherein

X represents $C_{1-4}$ alkyl, n represents 1, 2, 3 or 4, $R^1$ and $R^2$ each independently represents $C_{1-6}$ alkyl, $C_{2-4}$ alkenyl, $C_{2-6}$ alkynyl, $C_{3-8}$ cycloalkyl, aryl which may optionally be substituted wherein the substituent is at least one radical selected from the group consisting of halogen, $C_{1-4}$ alkyl, $C_{1-2}$ haloalkyl, $C_{1-2}$ haloalkoxy, $C_{1-2}$ haloalkylthio, acyl, nitro and cyano or aralkyl optionally substituted by halogen or $R^1$ and $R^2$ form, together with the N-atom to which they are bonded, a cyclic ring which may be substituted.

2. A compound according to claim 1, wherein

X represents methyl or ethyl, n represents 1 or 2, $R^1$ and $R^2$ each independently represents $C_{1-4}$ alkyl, $C_{3-4}$ alkenyl, $C_{3-5}$ alkynyl, cyclopropyl, cyclopentyl, cyclohexyl, phenyl which may optionally be substituted wherein the substituent is at least one radical selected from the group consisting of fluorine, chlorine, bromine, methyl, ethyl, n-propyl, trifluoromethyl, difluoromethoxy, trifluoromethoxy, trifluoromethylthio, acetyl, nitro and cyano or benzyl which may be substituted by chlorine, or $R^1$ and $R^2$ form, together with the N-atom to which they are bonded, a 5- or 6-membered cyclic ring optionally substituted by methyl, or a benzo-condensed cyclic ring thereof.

3. A compound according to claim 1, wherein

X represents methyl, n represents 1 or 2, $R^1$ and $R^2$ each independently represents ethyl, n-propyl, isopropyl, n-butyl, isobutyl, sec-butyl, allyl, propargyl, 1-methyl-2-propynyl, 1,1-dimethyl-2-propynyl, cyclopropyl, cyclohexyl, phenyl which may be substituted wherein the substituent is at least one radical selected from the group consisting of fluorine, chlorine, bromine, methyl, trifluoromethyl, difluoromethoxy, trifluoromethoxy, trifluoromethylthio, acetyl, nitro and cyano, or benzyl which may be substituted by chlorine, or $R^1$ and $R^2$ form, together with the N-atom to which they are bonded, 1,2,3,4-tetrahydroquinolin-1-yl or 1,2-dihydroquinolin-1-yl which may be substituted by methyl.

4. A compound according to claim 1, wherein such compound is $$\text{(31)}$$

5. A compound according to claim 1, wherein such compound is

(32) 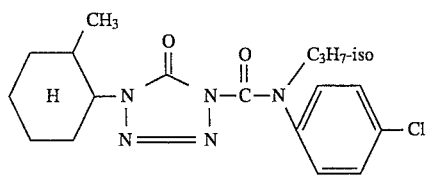

6. A compound according to claim 1, wherein such compound is

(38) 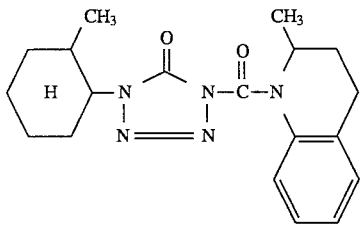

7. A compound according to claim 1, wherein such compound is

(81) 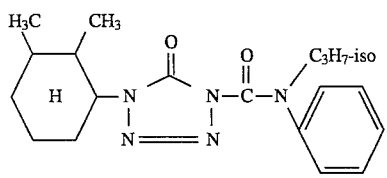

8. A compound according to claim 1, wherein such compound is

(83) 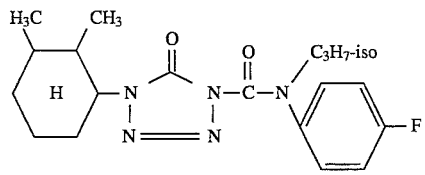

9. A method of combating unwanted vegetation which comprises applying to such vegetation or to a locus from which it is desired to exclude such vegetation a herbicidally effective amount of a compound according to claim 1.

10. The method according to claim 9 wherein such compound is

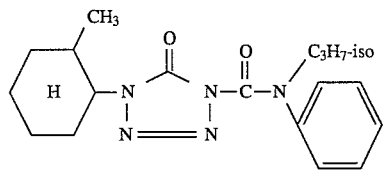

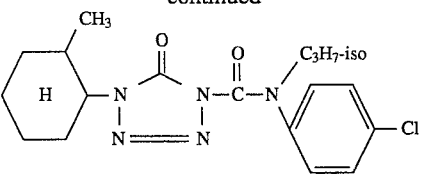

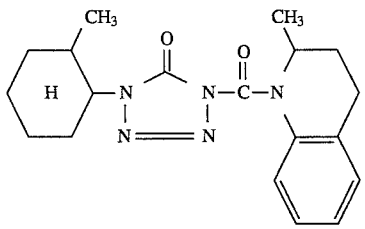

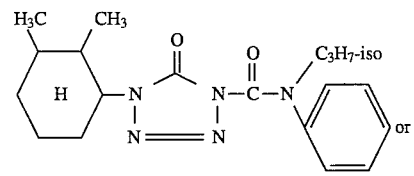

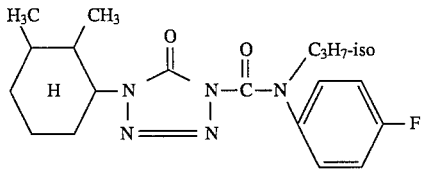

11. A herbicidal composition comprising a herbicidally effective amount of a compound according to claim 1 and a diluent.

12. A herbicidal composition comprising a herbicidally effective amount of a compound according to claim 1 and a synergistically effective amount of a further herbicide.

13. A tetrazolinone of the formula (II) 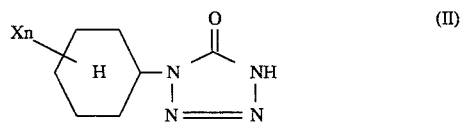

wherein

X represents $C_{1-4}$ alkyl, and n represents 1, 2, 3 or 4.

* * * * *